(12) United States Patent
Carpentier et al.

(10) Patent No.: US 10,987,524 B2
(45) Date of Patent: Apr. 27, 2021

(54) INTERSTITIAL ULTRASONIC DISPOSABLE APPLICATOR AND METHOD FOR TISSUE THERMAL CONFORMAL VOLUME ABLATION AND MONITORING THE SAME

(71) Applicants: Vermon S.A., Tours (FR); Institut National de la Sante et de la Recherche Medicale (INSERM), U1032, Paris (FR); Universite Pierre Et Marie Curie (Paris 6), Paris (FR); CarThera S.A.S., Paris (FR)

(72) Inventors: Alexandre Carpentier, Paris (FR); An Nguyen-Dinh, La Riche (FR); Jean-Yves Chapelon, Villeurbanne (FR); Rémi Dufait, Tours (FR); Christophe Notard, La Croix EnTouraine (FR); Françoise Chavrier, Chezeneuve (FR); Cyril Lafon, Tossieu (FR); Michael Canney, Lyons (FR); William Apoutou N'Djin, Lyons (FR)

( * ) Notice: Subject to any disclaimer, the term of this patent is extended or adjusted under 35 U.S.C. 154(b) by 0 days.

(21) Appl. No.: 15/789,426

(22) Filed: Oct. 20, 2017

(65) Prior Publication Data
US 2018/0036558 A1 Feb. 8, 2018

Related U.S. Application Data

(63) Continuation of application No. 13/794,347, filed on Mar. 11, 2013, now abandoned.

(51) Int. Cl.
*A61N 7/02* (2006.01)
*A61N 7/00* (2006.01)

(52) U.S. Cl.
CPC .............. *A61N 7/02* (2013.01); *A61N 7/022* (2013.01); *A61N 2007/0043* (2013.01);
(Continued)

(58) Field of Classification Search
CPC .. A61N 7/02; A61N 7/022; A61N 2007/0043; A61N 2007/0078
See application file for complete search history.

(56) References Cited

U.S. PATENT DOCUMENTS 6,267,726 B1 * 7/2001 Grimm .............. A61B 1/00142
600/459
2005/0124884 A1 6/2005 Bolorforosh et al.
(Continued)

FOREIGN PATENT DOCUMENTS

WO 2012066477 A1 5/2012

OTHER PUBLICATIONS

The State Intellectual Property Office of the People's Republic of China,, Second Office Action issued in corresponding Application No. 2014800241237, dated Dec. 3, 2018. (English translation not available.).

*Primary Examiner* — William J Levicky
(74) *Attorney, Agent, or Firm* — Stites & Harbison, PLLC; Jeffrey A. Haeberlin

(57) ABSTRACT

An interstitial ultrasound thermal ablation applicator for conformal treatment of an inhomogeneous tumor lesion includes: a body having a longitudinal axis; and a plurality of array transducers mounted on the body, arranged side by side and having azimuth directions parallel to the longitudinal axis of the body, and having outer faces disposed in a polygonal arrangement; the plurality of array transducers having predetermined elevation dimensions defined for directing emitted ultrasonic energy to obtain a conformal volume treatment of the tumor lesions. An electronic driving method for driving an applicator having multiple independent transducer elements arranged in rows and columns includes: controlling focal parameters of each row and column of transducer elements; and controlling a contribu-
(Continued)

tion of each row and column of transducer elements in a manner to provide a conformal ablated volume.

7 Claims, 11 Drawing Sheets

(52) U.S. Cl.
CPC ............ *A61N 2007/0047* (2013.01); *A61N 2007/0078* (2013.01); *A61N 2007/025* (2013.01)

(56) References Cited

U.S. PATENT DOCUMENTS

| | | | | |
|---|---|---|---|---|
| 2007/0264732 | A1* | 11/2007 | Chen | A61B 1/041 600/459 |
| 2009/0069686 | A1* | 3/2009 | Daft | B06B 1/0292 600/459 |
| 2011/0040172 | A1* | 2/2011 | Carpentier | A61B 5/0068 600/439 |
| 2011/0257562 | A1* | 10/2011 | Schaer | A61N 7/022 601/2 |

\* cited by examiner

INTERSTITIAL ULTRASONIC DISPOSABLE APPLICATOR AND METHOD FOR TISSUE THERMAL CONFORMAL VOLUME ABLATION AND MONITORING THE SAME

CROSS-REFERENCE TO RELATED APPLICATIONS

This application is a continuation of prior application Ser. No. 13/794,347, filed Mar. 11, 2013, the entire disclosures of which is incorporated herein by reference.

STATEMENT REGARDING FEDERALLY SPONSORED RESEARCH OR DEVELOPMENT

Not applicable.

THE NAMES TO PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

The present invention relates generally to an ultrasound medical method and device for interstitial disposable use having multiple ultrasound capacitive micromachined ultrasonic transducers (CMUT) to thermally ablate a conformal volume lesion and to monitor the ablated volume with the same apparatus.

2. Description of Related Art

In recent advances of tumor treatments, surgical methods have progressed a great deal towards minimally invasive techniques to decrease operation morbidity, pain, and the duration of hospitalization for patients. Minimally invasive procedures such as endoscopy, endovascular surgery or percutaneous procedures can be accompanied with thermal or cryogenic therapies using probes/applicators that are inserted directly inside or are placed adjacent to the target tissue volume.

Radio Frequency (RF) ablation and Laser Interstitial Thermal Therapy (LITT) have been successfully employed to treat different types of metastasis/tumors under MRI guidance. Preliminary results demonstrate significant improvement of life expectancy, though the current devices cannot be used to create lesions that perfectly match the target volume. Since RF antennas or LITT devices use omnidirectional sources for heating the surrounding tissue, no focusing or steering of the energy radiating pattern can be done without mechanically moving the probe or treatment devices. Other drawbacks in RF and LITT hyperthermia treatments are overheating, which occurs for tissue in contact with or in close vicinity of the treatment device, lack of control in lesion homogeneity due to blood flow, and difficulty in real-time monitoring of the therapy.

In thermal ablation, body tissue is exposed to temperatures higher than 43° C. for a certain time to damage or kill living cells. High Intensity Focused Ultrasound (HIFU) and High Intensity Contact Ultrasound (HICU) are some types of thermal ablation techniques under investigation for several pathologies. Currently piezoelectric-based devices are widely used to locally heat malignant tissue. However, current piezoelectric-based HIFU/HICU applicators show undesirable effects and shortcomings such as local tissue overheating at the transducer tissue interface and lack of control for the treatment volume (risk of ablation of healthy tissue or under treatment). In particular, in brain therapies, the treatment of pathologic tissue (tumor) requires a small diameter needle shaped applicator (maximum 3-4 mm) to access the site of treatment with minimal damage to the surrounding tissue and interstitial procedures provide the advantage of more accurate control of the ablated volume as well as the assurance of avoiding damage for healthy tissue since the HIFU/HICU source is located at the center of the tissues to be ablated. Current surgical products for interstitial HIFU/HICU procedures exhibit limited ablation capability features (focusing, conformal volume) and all require an active cooling system to avoid overheating of tissue in contact with the ultrasound source and therefore cannot be placed in direct contact with biologic tissue. Finally, current products may not exhibit optimal MR compatibility since artifacts may occur due to the presence of air bubbles, metal parts etc.

The above described difficulties led to the need for the development of alternative methods and apparatus that can be used to produce more homogeneous lesions with conformal treatment volumes for tumors and having the capability of real time monitoring or the measuring of physical and/or physiological functions/parameters of the organ or ablated tissue during operation. Prior art references directed to conformal treatment and or combined treatment/monitoring procedures include the following relevant documents as follows.

European Patent Application Publication No. 0 643 982 A1 (Burdette et al.) and International Patent Application Publication No. WO2007/124458 A2 (Diederich et al.) relate to a device and a method for treatment of prostatic or uterine tissue. Typically the ultrasound transducers are mounted inside a delivery system housing that prevents the emitting devices from directly contacting the tissue during operation. Multi-segment transducers can be used and a combination of multiple transducer arrangements can provide focusing of the acoustic energy. Unfortunately, the apparatus as described still requires cooling fluid to be circulated inside said delivery system to regulate the temperature of the probe. Furthermore, no conformal volume treatment methodology is described therein.

Similarly, in International Patent Application Publication No. WO 2009/125002 A1 (Carpentier et al.), where a percutaneous MRI compatible probe is disclosed for medical systems, the probe is described comprising a longitudinal body to be inserted into the body and having a plurality of ultrasonic transducers designed for focused and non-focused therapeutic ultrasound with an aspiration channel passing through the probe body longitudinally. The transducers can be arranged both longitudinally and circumferentially. A fluid-based cooling system is provided to control the temperature of the device. While transducers can be easily arranged longitudinally to form a linear phased array in circumference, it is not clear how the probe can achieve any focusing since the number of sectors is limited and no indication is provided for making it. No detail is disclosed for conformal volume treatment and the probe still requires a cooling system.

In U.S. Pat. No. 7,494,467 (Makin et al.) an ultrasonic and RF combined medical system is disclosed. In some embodiments, imaging transducers are combined with therapy transducers to monitor the tissue ablated. However none of the embodiments described can produce conformal volumetric lesions and, furthermore, the design requires the apparatus to be rotated or moved to treat or monitor a volume.

U.S. Pat. No. 5,697,897 (Buchholtz et al.) describes a therapeutic endoscope having a single linear array ultrasonic transducer mounted in the longitudinal axis for treatment and diagnosis. In one embodiment, the diagnostic transducer can be separate from the one for therapy. The document disclosure is limited to one plane focusing and requires the apparatus to be rotated to achieve a volume treatment.

U.S. Patent Application Publication No. US WO 02/32506 A1 and U.S. Patent Application Publication No. US 2006/0206105 A1 (Chopra et al.) disclose a thermal therapy device using a multi-element ultrasound heating applicator. The ultrasonic applicator is located under an acoustic window. The ultrasonic transducer can be electronically activated to cover the geometry of the treated area in a 2D plane, and a volumetric lesion (3D) can be obtained by rotating or moving the apparatus. The applicator has the capability for varying the power and switching the frequency of each ultrasound element enabling the temperature to be adjusted both radially and along the length of the applicator. However, the frequency control is limited to switching between discrete frequencies within multiple narrowband harmonics of the fundamental.

U.S. Pat. No. 6,379,320 (Lafon et al.) describes an ultrasonic applicator for intra tissue heating wherein a planar emitting surface is provided within the applicator head and is separated from the tissue to be treated by a sealed membrane. The space between the ultrasonic device and the membrane is filled with liquid which also serves as temperature regulation for the applicator. The applicator has no focusing or steering capability, so the treatment volume will only be obtained by rotating the applicator on site.

European Patent Application Publication No. 1,090,658 (Rabiner et al.) discloses methods or structures which include improvements over the above application requirements. However a number of problems still remain unsolved regarding, specifically, a conformal volume treatment method, a dedicated ultrasonic thermal ablation device, and a method of making the same.

BRIEF SUMMARY OF THE INVENTION

It is an object of the invention to provide an improved ultrasonic thermal ablation applicator for treatment of inhomogeneous lesions and for conformal volume ablation using a particular configuration of ultrasonic transducers that allows interstitial use and direct contact of the ablation source and the tissue to be treated.

It is another object of the invention to provide an improved ultrasonic thermal ablation applicator having independent linear array transducer modules assembled side by side to form a cylindrical source and having a predetermined width to achieve smooth conformal volume ablation.

It is another object of the invention to provide an improved ultrasonic thermal ablation applicator having a broad bandwidth (e.g. 2-30 MHz) which can be used to modulate the driving frequency during thermal ablation procedures for conformal volume ablation.

It is further an object of the invention to provide an improved ultrasonic thermal ablation applicator for conformal volume ablation and having a hollow central canal that provides access to the pathological tissue and secondary to the treatment materials, and which can be used for delivering in situ drugs or imaging contrast agents.

It is still another object of the invention to provide an improved ultrasonic thermal ablation applicator and method for limiting the number of electrical interconnections when focusing and steering the ultrasound energy in the region of interest/treatment.

It is another object of the invention to provide an improved ultrasonic thermal ablation applicator and method wherein both the alternating and direct excitation voltages can be independently modulated to control both the magnitude and spatial characteristics of the acoustic output of the device.

It is another object of the invention to provide a manufacturing method according to the said improved ultrasonic thermal ablation applicator wherein an inner removable rigid spindle or shaft is provided within the central hollow channel to rigidify the probe during its manufacturing/assembling and for tissue implantation.

It is another object of the invention to provide an improved ultrasonic thermal ablation applicator in direct contact with the tissues, wherein the transducer devices are equipped with integrated biosensors for monitoring the metabolic status of the tissue before treatment.

It is another object of the invention to provide an improved ultrasonic thermal ablation applicator in direct contact with the tissues, wherein the transducer devices are equipped with integrated nano laser oscillator emitters to allow in vivo sub-cellular tissue identification by near-infrared multi photon-induced auto fluorescence microscopy, and to allow photo sensitive nanoparticle delivery.

It is another object of the invention to provide an improved ultrasonic thermal ablation applicator in direct contact with the tissues, wherein the transducer devices are equipped with integrated temperature sensors and or integrated pressure sensors and or microelectrodes for monitoring the physiological functions of the organ during treatment.

It is another object of the invention to provide an improved ultrasonic thermal ablation applicator in direct contact with the tissues, wherein the transducer devices perform Doppler imaging of the tissue vascularization before and after the treatment for a revascularization efficacy proof.

According to one aspect of the invention, an interstitial ultrasound thermal ablation applicator to be inserted into an inhomogeneous tumor lesion for conformal treatment of the tumor lesion, includes: a body having a longitudinal needle shape and a longitudinal axis; and a plurality of array transducers externally mounted on said body, arranged side by side and having azimuth directions parallel to the longitudinal axis of the body, and having outer faces disposed in a polygonal arrangement. The plurality of array transducers have predetermined elevation dimensions defined for directing emitted ultrasonic energy to obtain a conformal volume treatment of the tumor lesion.

In one implementation, the plurality of array transducers are for emitting sound waves at a predetermined ultrasonic frequency, wherein the sound waves emitted from the plurality of array transducers at the predetermined ultrasonic frequency have a standard wavelength as measured in water as a propagation medium, and wherein an elevation dimension of the plurality of array transducers does not exceed three (3) standard wavelengths of the emitted sound waves at the predetermined ultrasonic frequency as measured in water as the propagation medium.

In another implementation, the plurality of array transducers consists of eight to twelve array transducers.

In yet another implementation, each of the plurality of array transducers includes an emitting surface covered with an electrically insulating protective layer such that the interstitial ultrasound thermal ablation applicator can be placed in direct contact with the tissue. Alternatively, a biocompatible protection film may cover the body and the plurality of array transducers.

In still yet another implementation, interstitial ultrasound thermal ablation applicator may further include an integrated Lab-on-Chip (LoC) device located within a surface of one of the plurality of array transducers for in-situ analyzing of tissue.

Advantageously, the plurality of array transducers may be capacitive micromachined ultrasonic transducer (CMUT) array transducers.

The body may further define a hollow central channel along the longitudinal axis, the hollow central channel serving as a passage for biopsy needles or tools for aspiration of biologic materials or providing in-situ drug delivery.

The applicator may have a diameter of 3 mm-4 mm, so as to not damage healthy tissue during insertion.

Further, the plurality of array transducers may have a thickness of less than 100 microns, and are flexible so as to conform an external surface of the body.

Other features and advantages of the invention will be set forth in, or apparent from, the detailed description of exemplary embodiments of the invention found below.

DETAILED DESCRIPTION OF EXEMPLARY EMBODIMENTS OF THE INVENTION

Figure 1A:
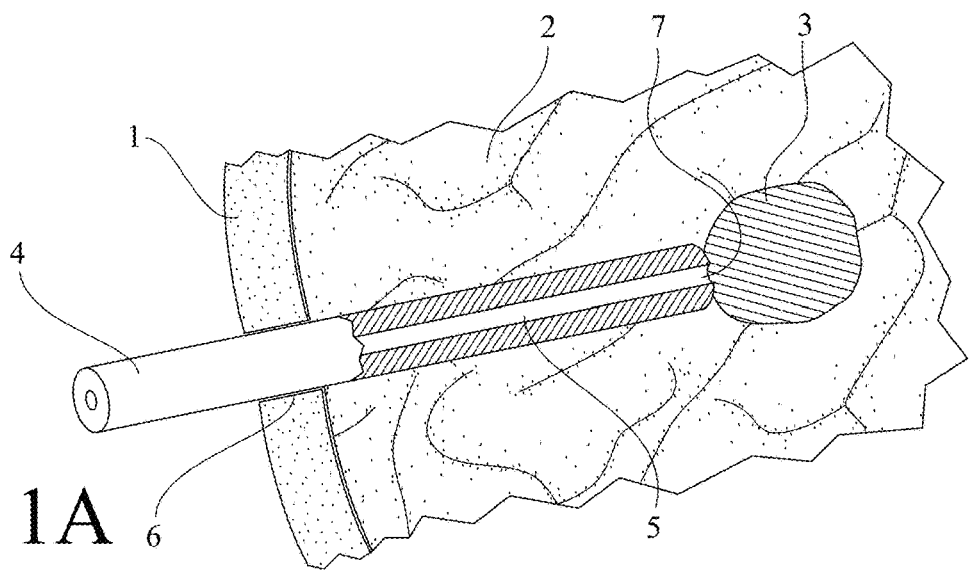
FIGS. 1A, 1B, and 1C are a sequence of figures illustrating an exemplary procedure for tumor interstitial treatment according to the invention.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed subject matter.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The terms "array transducer" or "transducer array" are used herein to describe a transducer device obtained by geometric arrangement of a plurality of individual transducers (i.e., transducer elements) having dimensions compatible with desired ultrasonic beam focusing and steering features.

The term "linear array" is generally used to describe a one-dimensional array and can be applied to arrays with flat or curved shapes.

The terms "element transducer" or "transducer element" or "transducer" are used herein to describe an individual ultrasonic transducer component of an array transducer. Generally, an element transducer of an array transducer has planar dimensions suitable for electronic steering and focusing of ultrasonic beams.

The present invention relates to a method and an apparatus for thermal conformal ablation. It should be noted that the invention is not limited to the description or arrangement illustrated in the accompanying drawings and description. It is also understood that any embodiments can be combined with the other embodiments or can be implemented into other apparatus with no change in the principle. Another major aspect of the present invention relates to the compatibility of the ablation device to be used under MRI imaging/monitoring with acceptable artifacts; this will be performed by the utilization of non-metallic materials and absence of air volume within the device body.

Figure 1B:
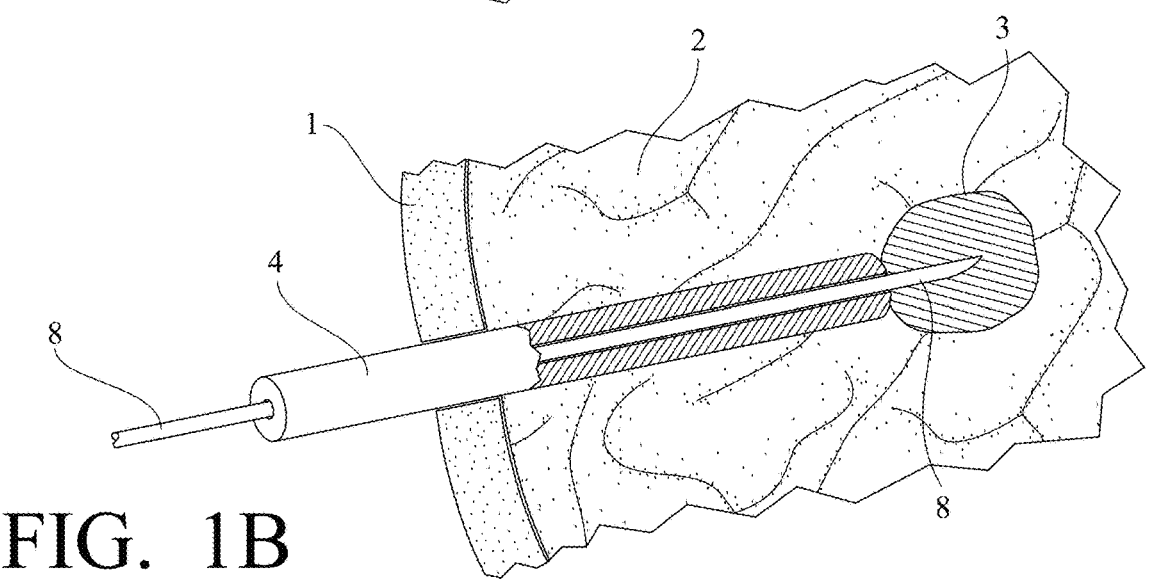
Figure 1C:
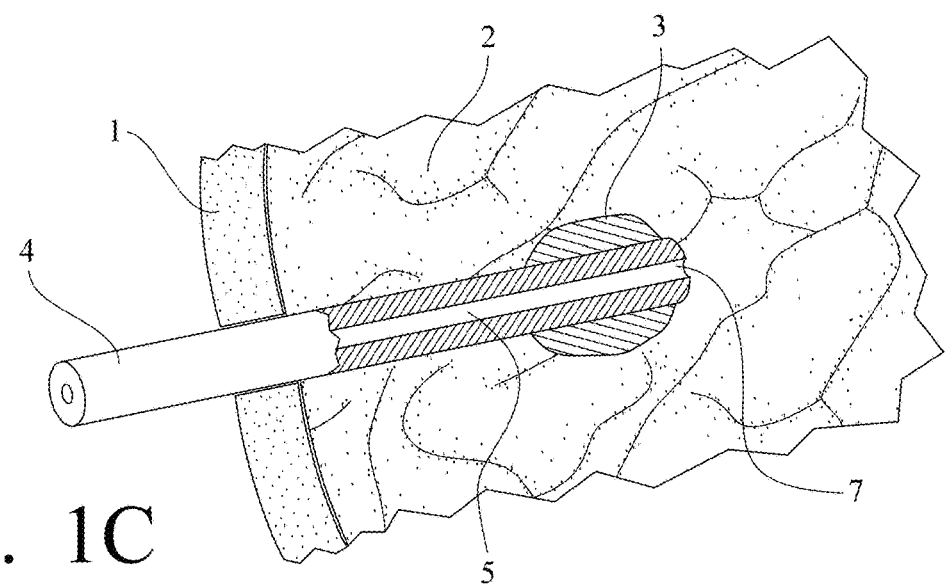

Referring to the method of the invention, the embodiment of FIGS. 1A, 1B, and 1C illustrate steps of an interstitial thermal ablation procedure by high intensity focused ultrasound (HIFU) or high intensity contact ultrasound (HICU) that can be used to treat cancerous or non-cancerous tumors and more particularly can be advantageously applied to brain tumor treatment. With HIFU, the therapeutic depth depends on the exposure conditions in general but more particularly on the operating frequency. Broadband CMUT transducers are advantageous as they allow performing conformal ablation by adjusting the depth of treatment with the operating frequency. cMUT transducers allow using Frequency Modulation (FM) strategies over a broad continuous spectrum (e.g. 2-30 MHz) for precise optimization of the ultrasonic frequencies as a function of the targeted tissue depths. Multiple independent broadband cMUT elements integrated on the same applicator allow combining multiple ultrasound beams at various frequencies over a broad continuous spectrum (e.g. 2-30 MHz) for performing conformal thermal ablation. Adjuvant drug delivery can also be achieved with CMUT transducers emitting low frequency waves.

FIG. 1A shows a thermal ablation applicator 4 inserted into brain tissue 2 by hole 6 created through a skull 1. The applicator 4 penetrates the brain tissue 2 to reach a malignant tumor 3 to be treated. The applicator 4 defines a hollow channel 5 and an opening 7 located at the distal end of the applicator 4. The hollow channel 5 has a diameter that is large enough to accommodate a diameter of a biopsy mandrel 8 (FIG. 1B). Alternately, the applicator 4 can be inserted into the brain tissue 2 with the biopsy mandrel 8 (FIG. 1B) in position in a manner to provide more stiffness to the applicator 4.

FIG. 1B shows a biopsy mandrel 8 inserted into the malignant tumor 3 for tissue extraction or analysis.

FIG. 1C shows the applicator 4 inserted through the malignant tumor 3. Preferably, the applicator is inserted without moving the biopsy mandrel such that a tumor sample is then trapped into the biopsy mandrel 8. The biopsy mandrel 8 is then removed from the applicator for tissue extraction or analysis without further moving the applicator. In addition, by removing the biopsy mandrel 8, the biopsy mandrel 8 will not disturb (i.e., create artifacts) the monitoring of the malignant tumor 3 under Magnetic Resonance Imaging (MRI) for upcoming treatment. After checking for proper positioning of the applicator 4 by a new MRI sequence, a treatment simulation is performed and, further, the treatment itself started.

The medical procedure as depicted in FIGS. 1A, 1B and 1C is well adapted for brain tumor treatment since the diameter of the applicator 4 remains reasonable (3 mm-4 mm) and the applicator 4 is MRI compatible. Furthermore, the hollow channel 5 enables physicians to extract ablated tissue from the tumor. Once the treatment procedure is complete and monitored with MRI or ultrasonic imaging, an aspiration of a liquefied portion of treated tissue can be drawn through the hollow channel 5 from the opening 7 of the applicator 4. At the end of the procedure, the applicator 4 is removed from the brain tissue 2 and a stitch is performed on the skin for closing.

For carrying out the medical procedure as explained in FIG. 1A to FIG. 1C, the applicator 4 is equipped with a plurality of ultrasonic array transducers arranged and symmetrically disposed around and along a longitudinal axis of the applicator 4 to provide a 360 degree ultrasonic sonication. Such an applicator 4 suitable for treatment of a malignant tumor 3 will be further described in more detail below. The applicator 4 and method use multi-focused ultrasound to obtain a conformal volume treatment of tumor tissue regions.

Figure 2:
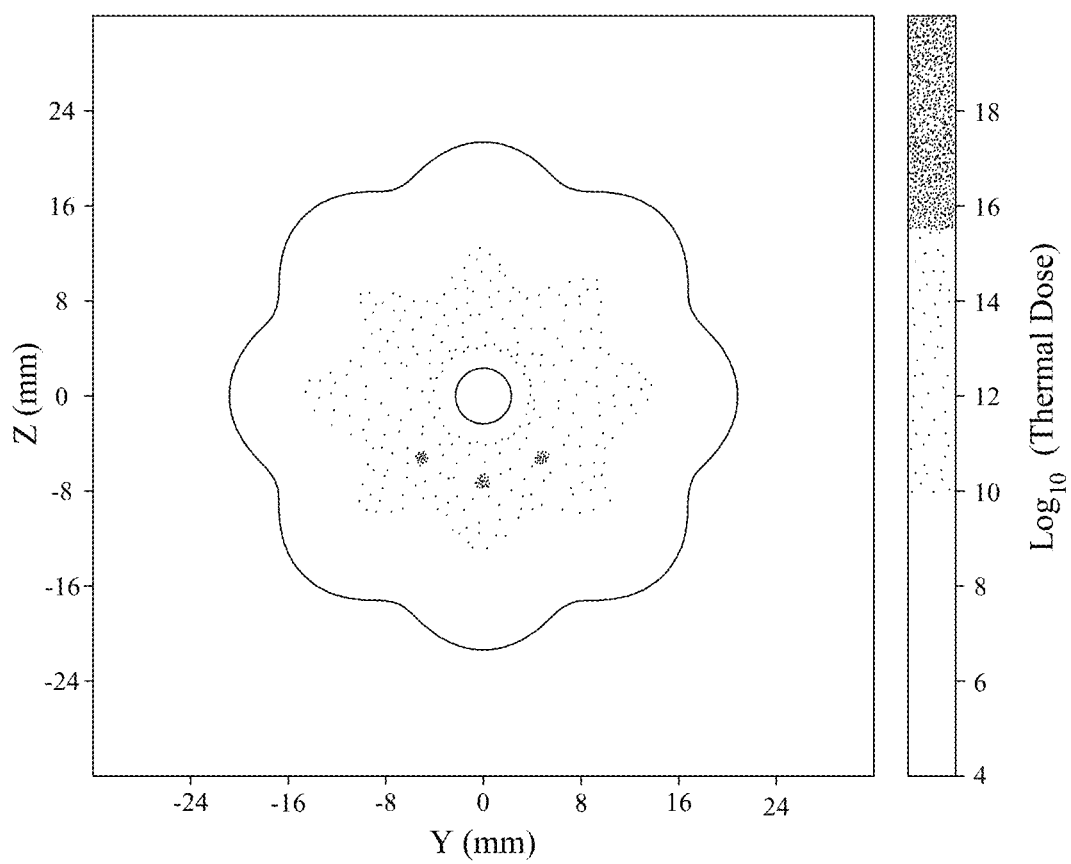
FIG. 2 is a graphical view of a section of a treatment volume of a conformal lesion.

FIG. 2 is a graph of a numerical modeling performed using an exemplary applicator having eight faces in a polygonal arrangement. As shown in FIG. 2, a smooth volume can be achieved by using independent control of the arrays and taking into account the acoustic absorption and thermal conductivity of the tissue, and lesion boundary conditions.

Figure 12:
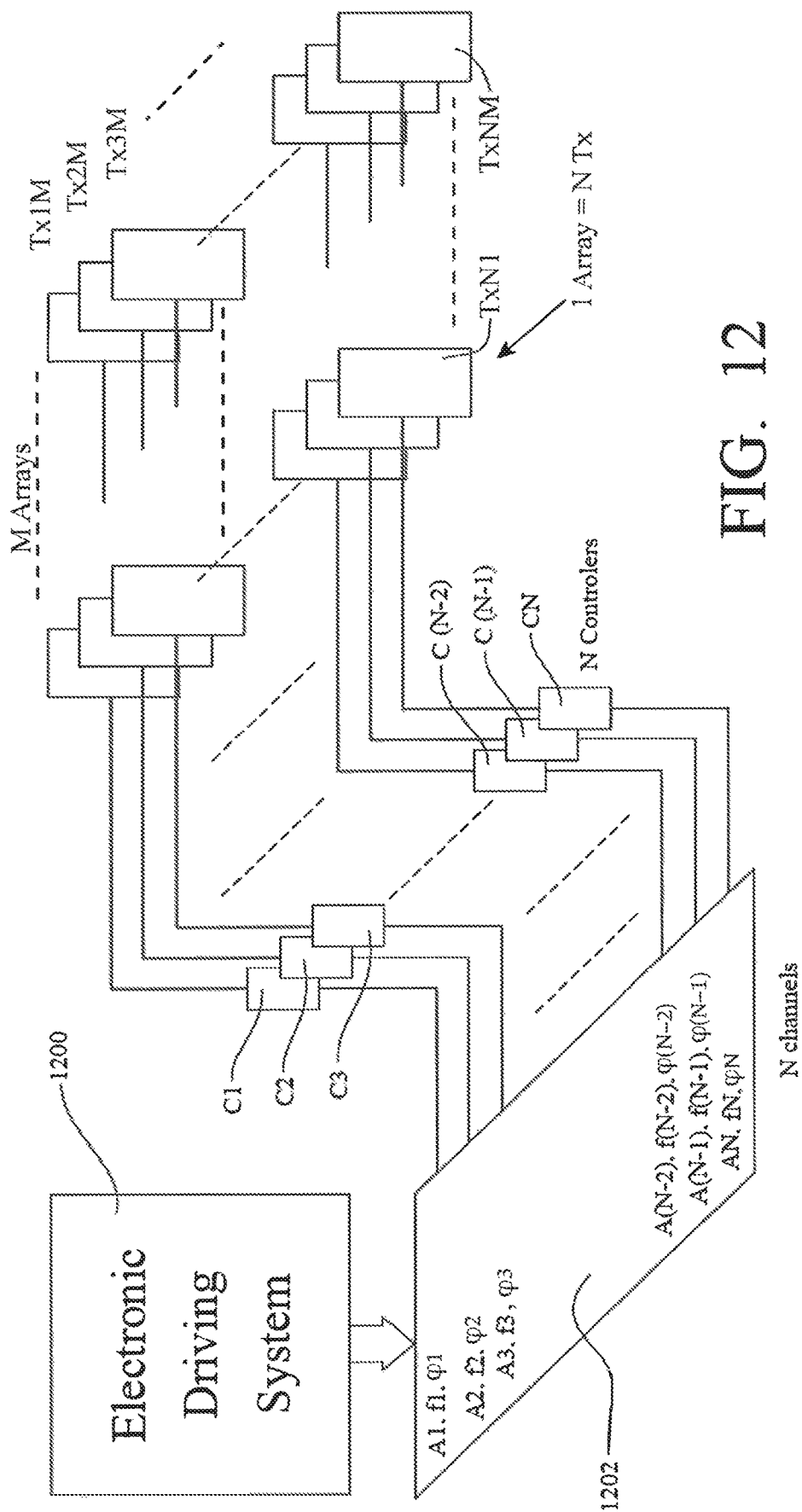
FIGS. 12, 13A, and 13B are functional block diagrams of an electrical system of an interstitial ultrasonic disposable applicator, according to the invention.

As shown in FIG. 12, each transducer Tx1, Tx2, Tx3, Tx(N-2), Tx(N-1), TxN is connected to independent driving electronics (i.e., controllers) C1, C2, C3, . . . C(N-2), C(N-1), CN that may consist of electrical impedance matching networks and DC bias controller, and which may be controlled by a system mainframe 1200 in communication with an output power management system 1202 that controls the amplitude ($A_N$), frequency ($f_N$) and phase ($\varphi N$) for each individual element for electronic focusing or steering. As shown schematically, the configuration is repeated for M arrays.

Figure 13A:
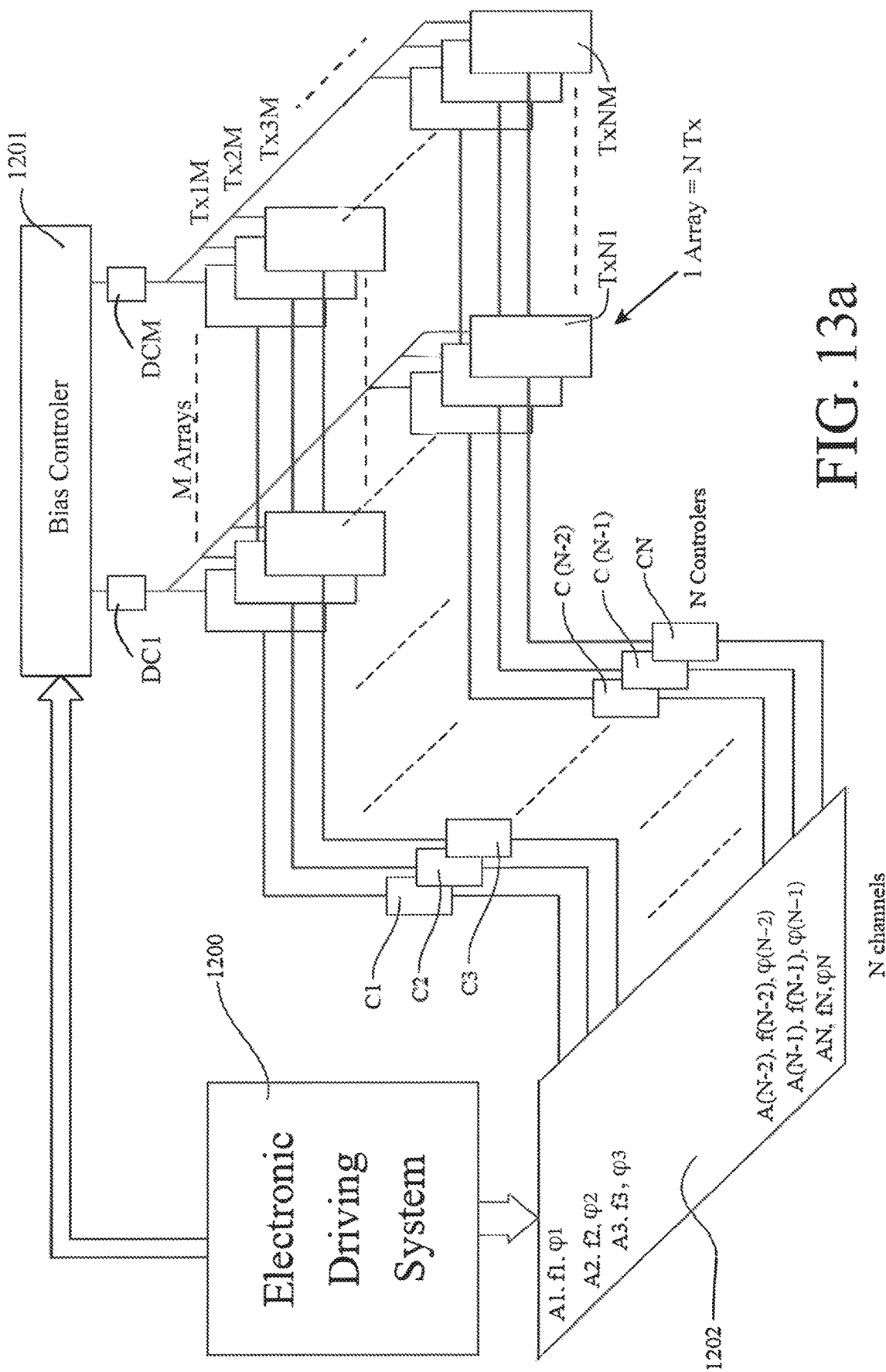
Figure 13B:
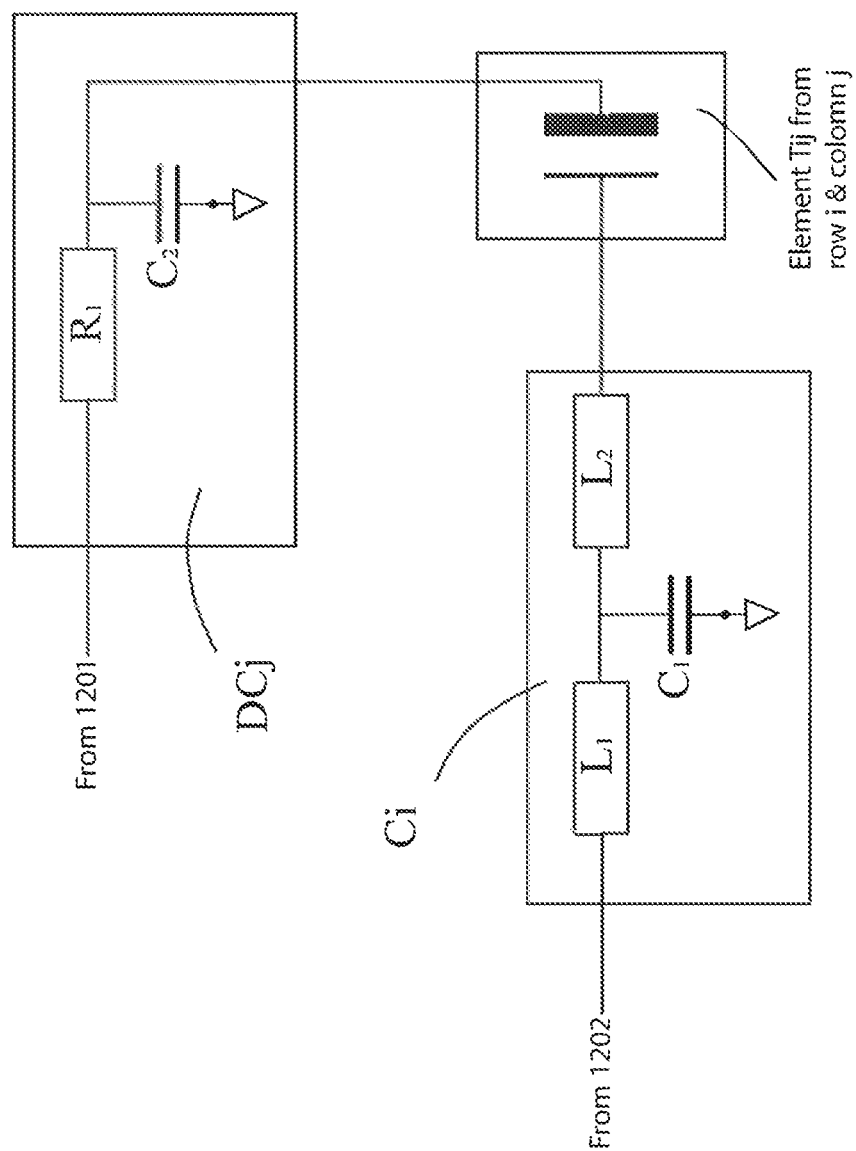

In another configuration, as shown in FIG. 13a, the electronic driving system may include a separate DC bias controller 1201 for activation of specific subgroups of elements or arrays of the device that allows for a row-column control system. In this configuration, the DC bias voltage level delivered to a specific subgroup of elements may be used to modulate the acoustic output of a specific subgroup of elements that have a common bottom electrode. To achieve this configuration, the elements are wired electrically according to the configuration shown in FIG. 13b, where the AC driving voltage is applied at the top electrode to a single element or group of elements and the DC bias voltage is applied at the bottom electrode. In this configuration, the bottom electrode may be common to a single element, several elements, one entire linear array of the transducer, or to all of the elements of the transducer.

The advantage of using a CMUT device for high intensity ultrasound is its intrinsic absence of self-heating during long (several seconds to several minutes) and continuous driving operations. Indeed, electrostatic vibration forces created by capacitive membranes are based on voltage variations with no need for current intensity. Since a cavity gap is vacuum sealed, low parasitic capacitance is expected so a self-heating effect is therefore negligible as well.

Figure 7:
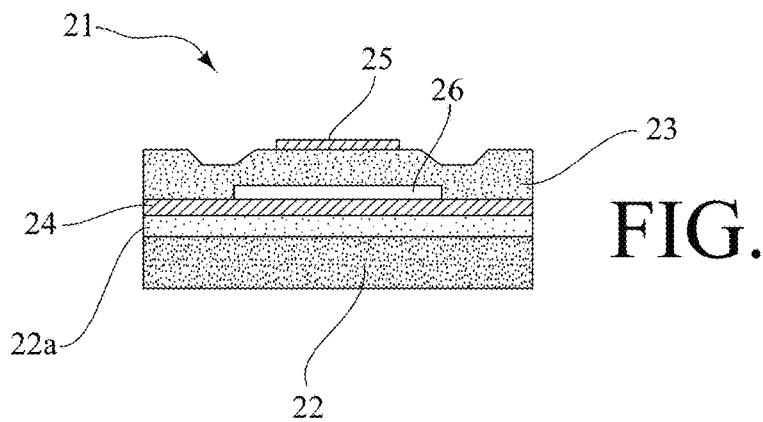
FIG. 7 is a side sectional view of an internal structure of an exemplary capacitive micromachined ultrasonic transducer (CMUT), according to the invention.

FIG. 7 is a sectional view of an exemplary CMUT cell 21, which is described in more detail below.

Figure 3:
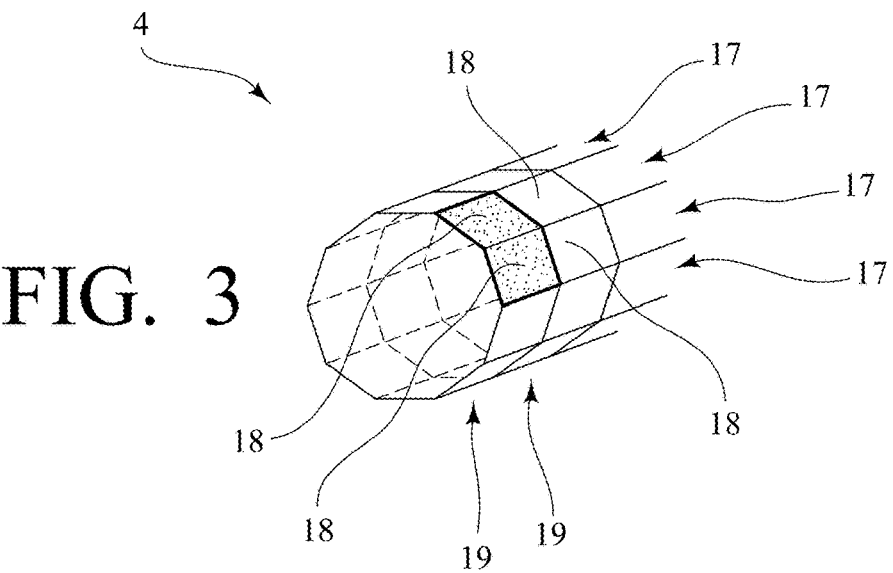
FIGS. 3, 4, and 5 show several embodiments of an exemplary interstitial ultrasound thermal ablation applicator according to the invention.
Figure 4:
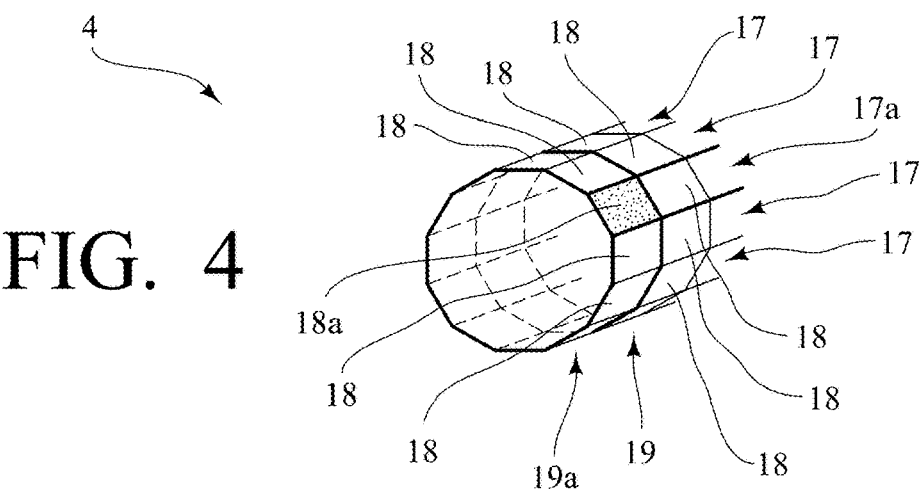
Figure 5:
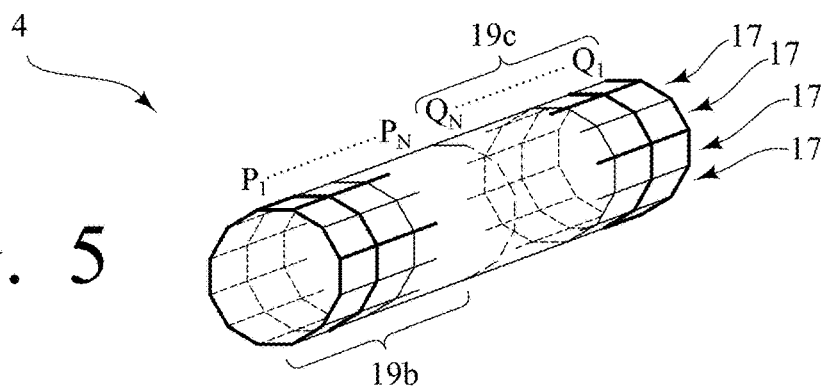

FIGS. 3, 4 and 5, show exemplary configurations for array transducers (e.g., FIG. 12, Tx1, Tx2, Tx3, Tx(N-2), Tx(N-1), TxN, for M arrays) mounted on an exemplary thermal ablation applicator 4 (see FIG. 1A-FIG. 1C) to perform conformal volume ablation. The purpose of this array configuration is to achieve optimal tissue ablation efficiency under accurate volume control while limiting the number of independent driving channels at reasonable numbers (e.g., 64) for mastering of cost and design complexity.

As a non-limiting example, FIG. 3 shows an array configuration of the thermal ablation applicator 4 comprising an assembly of ten transducer arrays 17 (i.e., columns of transducer elements 18, also referred to as array transducers) arranged in a polygonal manner. Each of the transducer arrays 17 preferably includes a plurality of transducer elements 18, which can be either identical to each other or under customized specifications with no change in principle. Preferably, all of the transducer arrays 17 are identical geometrically and, for simplicity, the transducer elements 18 operate at a resonance frequency that maximizes a ratio between output energy and penetration. For example, an optimal frequency range is from about 3 to 10 MHz and an optimal acoustic surface intensity is between about 10-30 watts/cm$^2$ for a tumor having a diameter of around 30 mm. Such frequency range and output acoustic intensity are here given as an example and should not be considered as design limitations for the present invention, as other combinations of frequency/intensity may be applied to the description of the invention with no change in the principle thereof.

Still referring to the array configuration of FIG. 3, the transducer elements 18 are electrically connected or shunted by pair (two adjacent transducer elements 18 are to be connected together) in a transverse sectional plan of the applicator 4, as highlighted in the figure. The shunting of adjacent transducer elements 18 reduces the number of active channels while keeping smooth polygon angles for the applicator 4. As is shown, the applicator 4 comprises a plurality of rows 19 of transducer elements 18, each of the rows 19 of transducers formed by several transducer elements 18 shunted two by two in order to reduce the number of connections. For clarity of the description, the applicator of FIG. 3 is preferably composed of ten transducer arrays 17 (i.e., columns of transducer elements) and twelve rows 19 of transducer elements (not all shown). The number of transducer arrays 17 equates to the number of transducer elements 18 in each row 19. As the adjacent transducer elements 18 in each row 19 are shunted two by two, the number of electrical connections is reduced to sixty instead of one hundred twenty.

FIG. 6A through FIG. 6D are graphs of modeling results of conformal volumes obtained with a configuration of transducer arrays 17 mounted on an exemplary thermal ablation applicator 4, such as described above.

Figure 6A:
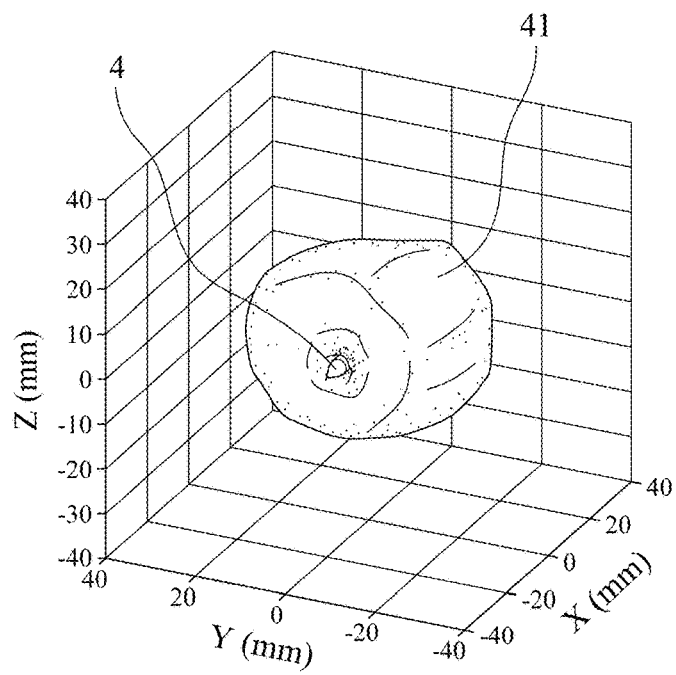
FIGS. 6A through 6D are graphical renderings of examples of 3D conformal volumes obtained using an exemplary thermal ablation applicator according to the invention.

FIG. 6A shows an example of a 3D complex volume 41 (i.e., heating volume shape or ablated lesion volume) that is obtained using such an applicator 4. In this example the acoustic power is independently programmed for each transducer element 18 (FIGS. 3-5) to achieved the desired 3D complex volume 41 (i.e., heating volume shape or ablated lesion volume).

Figure 6D:
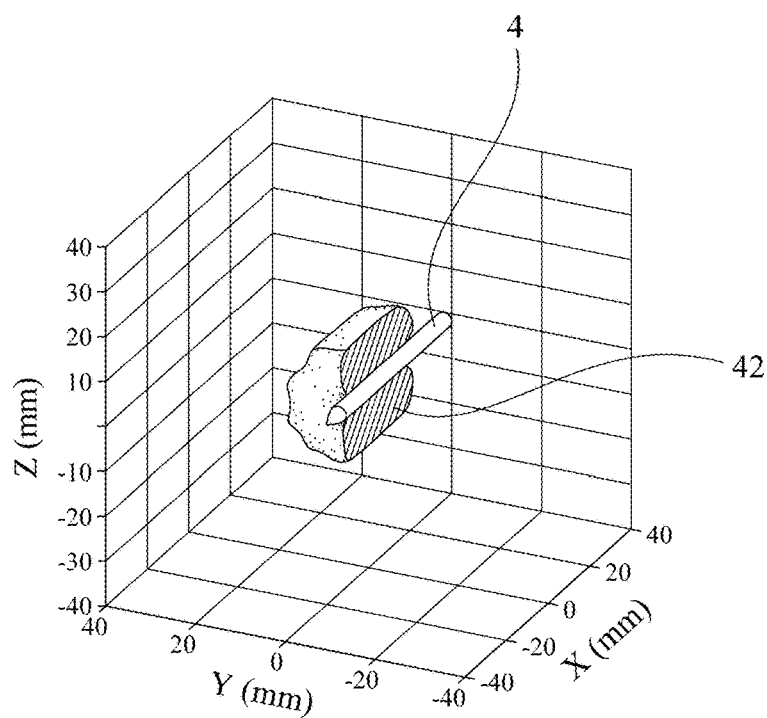
Figure 6B:
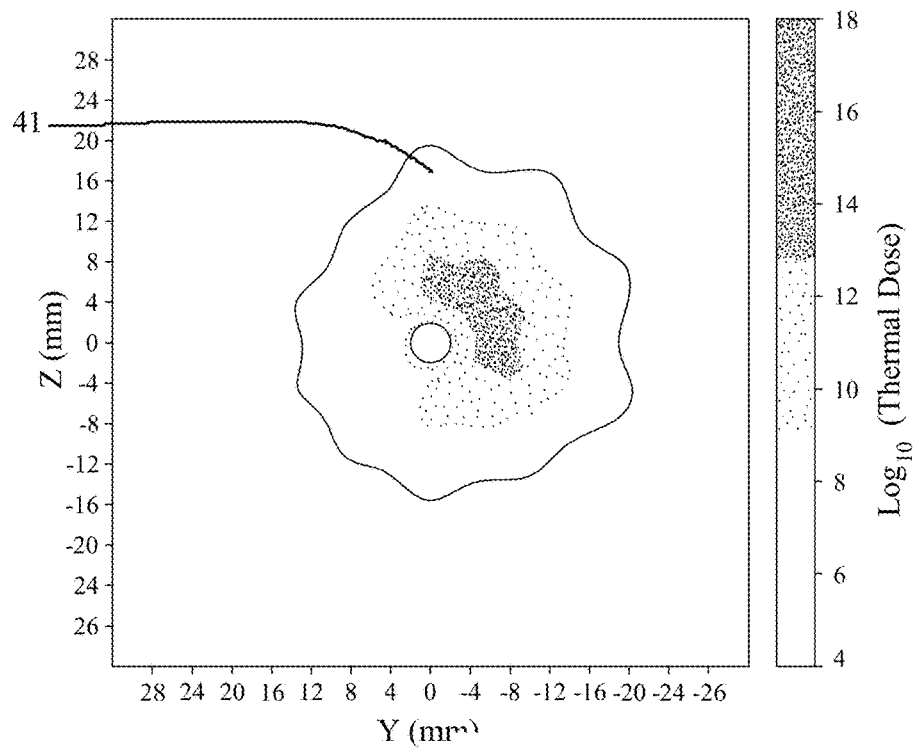

FIG. 6B is a sectional view of the exemplary ablated lesion volume 41 with thermal doses spreading around such an applicator 4. This graph clearly indicates the capability of such an applicator 4 to provide localized and well-controlled thermal dose distribution to lesion tissue in a 3D complex volume (i.e., heating volume shape).

Figure 6C:
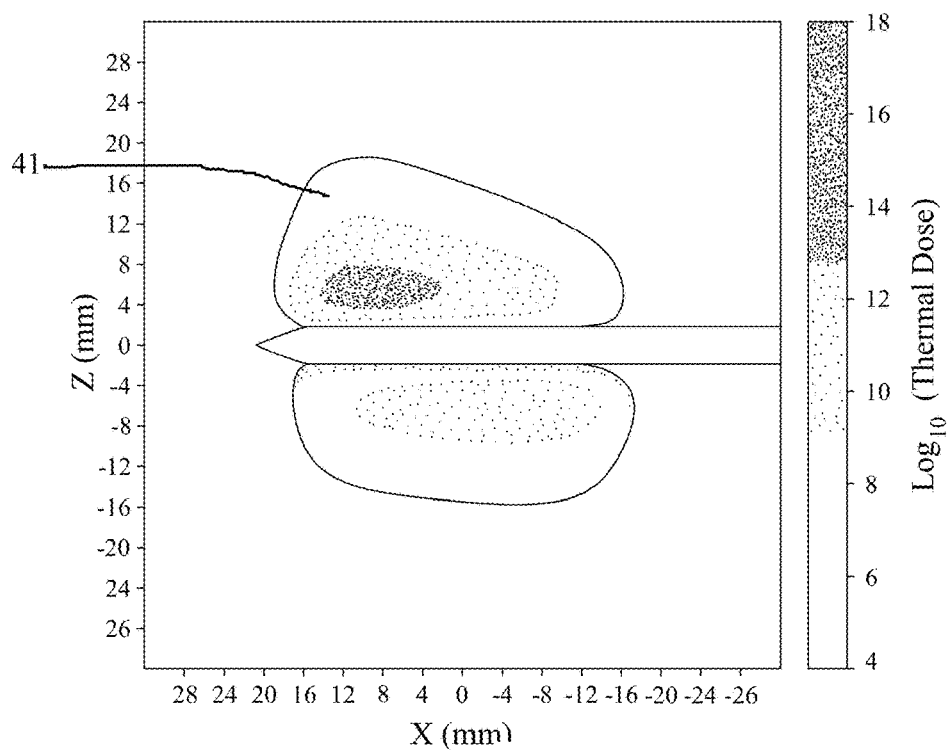

FIG. 6C is a longitudinal view of the exemplary ablated lesion volume 41 of FIG. 6B, showing thermal doses distribution around such an applicator 4. The asymmetrical distribution shown in this figure and in FIG. 6B illustrate conformal volume treatment.

FIG. 6D shows an example of a different 3D complex volume 42 that is obtained using such an applicator 4 with twelve (12) transducer arrays operated at 6 MHz. For better description of the volume treated, the illustration of FIG. 6D only shows the ½ volume with its symmetrical sectional face (the whole volume is to be considered when treated with all transducers in operation). An output acoustic power sufficient to generate a surface intensity of 20 W/cm$^2$ is applied at the surface of array transducer under the following sequence: 105 seconds ON.

The exemplary thermal ablation applicator 4 of the invention may also advantageously utilize continuous Frequency Modulation (FM) to control tissue penetration and thermal dose distribution since the CMUT operations are sensitive within a large frequency range. FM strategies can be applied on each electrically independent cMUT transducer to control ultrasonic frequencies over a broad continuous spectrum and achieve simultaneously various treatment depths in 3D. In other words, the transducers elements 18 and by extension the transducer arrays 17 can be excited at different frequencies so as to better fit tissue ablation requirements and conditions, or to emphasize the conformal effect by the possibility of applying a particular emitting frequency on each transducer element 18 or transducer array 17.

More particularly, as shown in FIG. 7, an exemplary CMUT cell 21 according to the invention includes a membrane 23 that is excited by oscillations of electrostatic forces exerted via a bottom electrode 24 and an opposing top electrode 25. The electrostatic forces are created by an electrical field exerted between the opposite electrodes 24 and 25 and a capacitance value is controlled by a gap of a sealed cavity 26 (i.e., a capacitance gap) these electrostatic forces are governed by the following equation $$Fe = -S_\varepsilon 0 V^2/z^2 \tag{1}$$

that can be developed to obtain $$Fe = -S\varepsilon 0 \frac{(V0+V1)^2}{z0^2(1+u1/z0)^2} \tag{2}$$

wherein V0 represents the DC voltage and V1 represents the AC voltage applied to the CMUT for oscillation; finally the previous equation can be developed into fundamental and harmonic terms as follows $$\frac{F}{S\varepsilon 0} = \frac{(V0)^2}{(z0)^2} + 2\frac{(V0V1)}{(z0)^2} + \frac{(V1)^2}{(z0)^2} + u1\frac{(V0)^2}{(z0)3} + \text{higher terms.} \tag{3}$$

Here one can see that the first term corresponds to the static force, the second term drives $$\left(2\frac{(V0V1)}{(z0)^2}\right) \tag{4}$$

the membrane in fundamental mode with a maximum of energy and the third and other higher terms contribute to harmonic modes, based on the above description it is important to notice that under absence of DC voltage (V0=0) only harmonic modes are excited and are much less energetic than the fundamental one. In transmission mode, excitation voltage oscillations are converted into alternative electrostatic forces to vibrate the membrane 23 (emission of ultrasonic waves). In receiving mode, mechanical forces applied on transducer cause the membrane 23 to deflect, move, or deform, and modify the gap of the sealed cavity 26. Then a voltage variation is measured between the bottom electrode 24 and the top electrode 25. The structure of the exemplary CMUT cell 21 desired is formed on a silicon substrate 22 (and an oxide layer 22a), but other materials such as glass or polymers may be utilized as a base structure as well. Other complementary layers can be added to the exemplary CMUT cell 21 to provide better protection or to improve acoustic performance of the structure. However, the operational principle of the CMUT cell 21 is substantially as described herein.

In another embodiment as shown in FIG. 4 an exemplary thermal ablation applicator 4 includes transducer arrays 17 (columns of transducer elements 18) and rows 19 of transducer elements 18, as in the embodiment of FIG. 3. However, in the embodiment of FIG. 4, the top electrodes (see FIG. 7, top electrode 25) of the endmost row 19a of transducer elements 18 are connected together. The bottom electrodes (see FIG. 7, bottom electrode 24) of the transducer elements 18 of a preselected transducer array 17a (i.e., column of transducer elements 18) are also connected together. Each of the transducer elements 18 (i.e., a CMUT cell 21 (FIG. 7)) needs to be polarized via its opposite electrodes to operate. Therefore, the control of a selected transducer element 18a on the exemplary thermal ablation applicator 4 is obtained by selecting the particular transducer array 17a (i.e., column) and the particular row 19a of transducer elements 18 of the selected transducer element 18a, and applying a voltage excitation function with suitable frequency (typically 6 MHz but can also be adjusted in the range of 3-10 MHz) and acoustic surface intensities (from 5 to 20 w/cm$^2$) across the corresponding bottom electrodes and top electrodes to produce the desired ultrasonic vibration effect.

The exemplary applicator 4 of FIG. 4 further has the top electrodes of each respective row 19 of transducer elements 18 connected together, and the bottom electrodes of each respective transducer array (i.e. column) of transducer elements 18 connected together. Advantageously, this array configuration reduces the number of connections required for polarization of individual transducer elements 18 to control the active surface of the applicator 4. Indeed, as operation in CMUT devices is governed by the bias voltage applied between the two opposite electrodes of the device as described in detail in the previous section relating to FIG. 7. This voltage will pre-stress the CMUT to react to any voltage variation by moving the membrane to modify the capacitance gap accordingly. This, consequently, also creates ultrasonic waves. For one skilled in the art, only the surface area of transducer that is covered by the involving bottom and top electrodes is energized or sensitive to mechanical pressure in receiving mode as previously explained. Thus, this structure and method enables control of any of the individual transducer elements 18 of the exemplary thermal ablation applicator 4 by applying suitable voltage to the corresponding top electrode 25 and bottom electrode 24 (see: FIG. 7). The number of control connections will then depend on the number of independent columns (n) (transducer arrays 17) and rows (m) (rows 19 of transducer elements 18) to be controlled. In other words, all of the transducer elements 18 of the array configuration can be individually address using n+m control connections instead of n×m control connections to connect each transducer element separately.

Similarly, FIG. 5 shows another exemplary thermal ablation applicator 4 which is composed of rows 19b on one end and rows 19c on the other end of the applicator 4. Rows 19b and rows 19c are symmetrically disposed with a symmetry line 20 defined at a middle of the exemplary thermal ablation applicator 4. Transducer arrays 17 (i.e., columns) are disposed as shown in previous illustrations of FIG. 3 and FIG. 4, and each transducer array 17 comprises aligned transducer elements 18 from all rows 19b and rows 19c. Optionally and as shown, adjacent transducer arrays 17 are electrically shunted two by two in order to reduce the number of output connections for the applicator. Rows 19b and 19c are arranged respectively in the position order from $P_1$ to $P_N$ for rows 19b and from $Q_1$ to $Q_N$ for rows 19c. Furthermore, the row of position $P_1$ is shunted to the row of position $Q_1$ to form a unique electrical connection and so on in manner to divide by two the number of output connections for rows 19b and 19c. In operation, the bottom electrodes of the CMUT cells of the respective transducer arrays 17 are connected together, and the top electrodes of the CMUT cells of the respective rows 19b and rows 19c are connected together, so that the control of the active surfaces of the exemplary thermal ablation applicator 4 is identical to control described with respect to the exemplary applicator of FIG. 4. Advantageously, the exemplary thermal ablation applicator 4 of FIG. 5 having transducer rows 19b and transducer rows 19c that can be excited in shunted mode two by two expands the ablation volume (especially in long axis dimension) that can be treated with a single applicator 4.

Figure 8A:
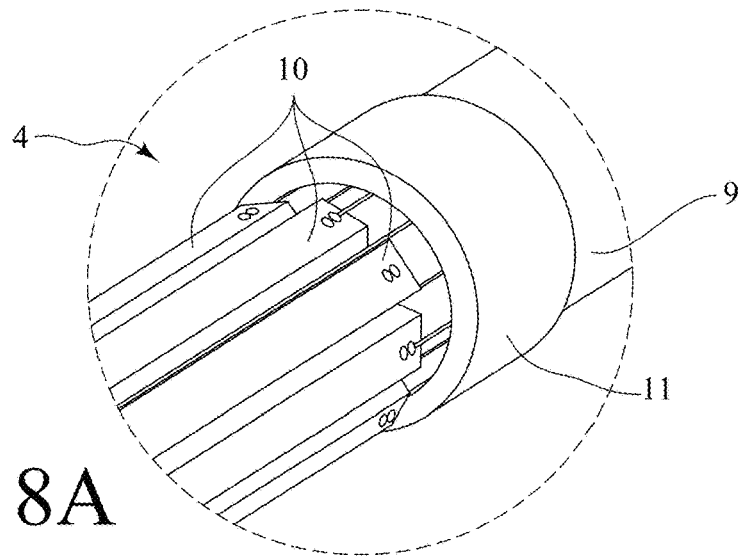
FIG. 8A is an enlarged view of a proximal end of the exemplary thermal ablation applicator as identified by the broken lines labeled 8A in FIG. 8.
Figure 8:
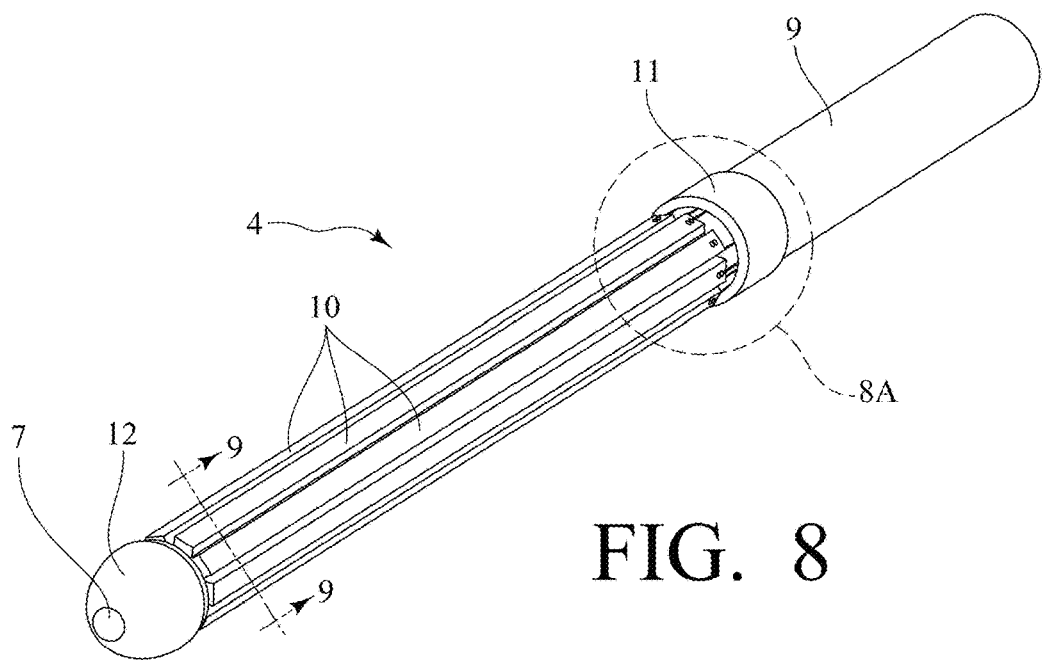
FIG. 8 is a perspective view of another embodiment of an exemplary thermal ablation applicator.
Figure 9A:
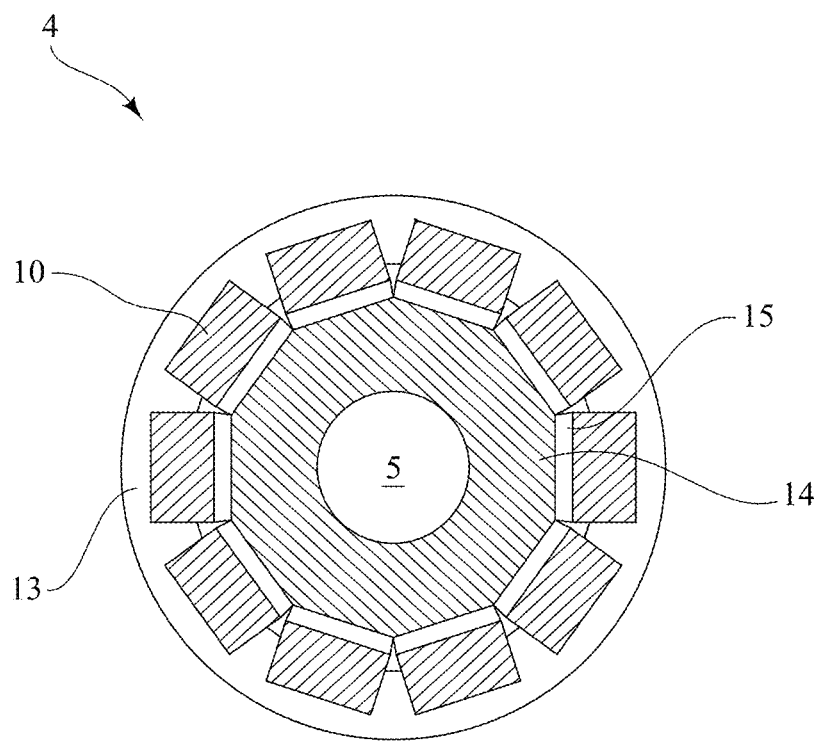
FIG. 9A is a sectional view showing one assembly of the exemplary thermal ablation applicator taken at the plane identified as 9-9 in FIG. 8.
Figure 9B:
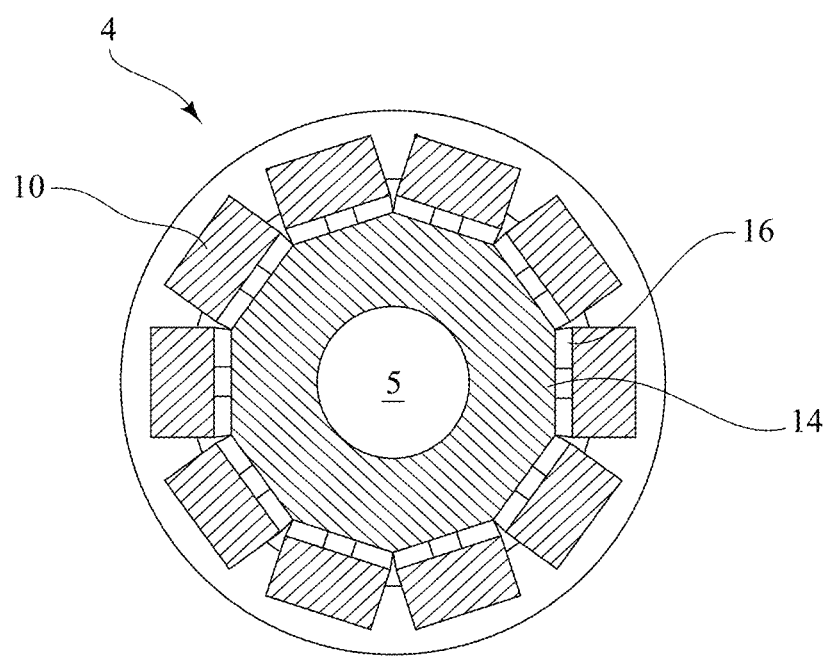
FIG. 9B is a sectional view showing another assembly of the exemplary thermal ablation applicator taken at the plane identified as 9-9 in FIG. 8.

FIG. 8 shows yet another embodiment of an ultrasonic thermal ablation applicator 4, including array transducers 10 comprised of CMUT (not shown) elementary transducers that are arranged along a long axis of the array transducers 10. The number of array transducers 10 of the thermal ablation applicator 4 is dependent on the application and type of tumor to be treated, and this number may extend from eight to twelve, typically, for achieving a reasonable compromise. Twelve array transducers 10 mounted on the periphery of the thermal ablation applicator 4 is preferable, but not so limited. Preferably, array transducers 10 are identical in shape and dimensions but may differ in CMUT arrangement on their active face. Array transducers 10 are electrically connected to flexible electrical collectors 9 that provide electric contacts of the CMUT elements to an external interface (not shown). Typically, a coaxial cable (not shown) is connected to interface with the system mainframe (not shown). The flexible electrical collectors 9 are preferably comprised of flexible PCB circuits using Kapton® or any polyimide-based material with a thickness thinner than 25 μm. As discussed below, the array transducers 10 may be assembled directly on an applicator body 14 as shown in FIG. 9A, or may be pre-assembled with a backing support 16 as shown in FIG. 9B prior to mounting on the applicator body 14. The backing support 16 can be made up of acoustic absorbent materials such as particle filled resin, plastic, ceramic, or any other nonmetallic (i.e., transparent to x-rays and other medical imaging radiation) acoustic absorbent material. At a distal end of the thermal ablation applicator 4, a guiding piece 12 in a substantially conical shape is provided as protection for the array transducer mounting. The guiding piece 12 has an opening 7 located at a center position in alignment with a hollow channel 5 (see: FIG. 1A-FIG. 1C) of the thermal ablation applicator 4. On the proximal end of the thermal ablation applicator 4 where the array transducers 10 terminate, a ring 11 is provided to secure an interface between the array transducers 10 and the flexible electrical collectors 9.

FIG. 8A shows a magnified view of the proximal end of applicator 4 where assembly details are provided for the array transducers 10, the ring 11, and the flexible electrical collectors 9. More particularly, the ring 11 is preferably mounted to the probe body or structure and secures a flex extension part in the vicinity of the array transducers 10. The flexible electrical collectors 9 can be made of thin polyimide PCBs (e.g., 12 µm thick polyimide film), with copper/gold plated tracks on one or both sides.

FIG. 9A is a sectional view of one assembly of the exemplary thermal ablation applicator 4 taken through plane 9-9 as shown in FIG. 8. The figure shows the assembly of array transducer components and construction details of the applicator 4 wherein a body 14 is provided with the hollow channel 5. The body 14 may have a plurality of faces regularly disposed on its periphery to form a polygon. In order to achieve a smooth treatment volume geometry, a number of faces for the body 14 may preferably range from eight units at a minimum and have an optimum number of twelve, however no limitation is made on the number of faces, as the number will only be limited by available miniaturization and integration process/technology. In the same spirit of design, a cylindrical shape for the body 14 is ideally desirable, but this inherently constrains the transducer to be made flexible and conformable at such a small diameter (3-4 mm). The array transducers 10 are disposed on external faces of the body 14 with optional acoustic absorbing material 15 that also comprises electrical contacts. The electrical contacts can be, for example, flexible printed circuit boards (flexible PCB), as the thickness of flexible PCBs is thin as compared to the other components. For clarity, for one skilled in the art, the flexible PCBs are sandwiched between the array transducers 10 and the external faces of the body 14. The optional absorbent material can be particle filled resins or rigid nonmetallic materials with high backscattering properties. Otherwise, the array transducers 10 may be directly secured to the body 14 with electrical contacts disposed there between. The array transducers 10 may be provided with a matching layer (not shown) laminated on a front surface to improve the acoustic performance and electrical safety for patients. Finally, the exemplary thermal ablation applicator 4 is covered with a protective layer 13 to complete the assembly. Advantageously, the protective layer 13 can be made up of electrically insulated silicon rubber or resin and preferably molded onto the thermal ablation applicator 4 to obtain a cylindrical external shape. As an alternative solution, a polygonal external section is also possible with the use of a flat thin electrically insulated protective layer that will be conformal to the front surfaces of the array transducers 10.

Figure 10:
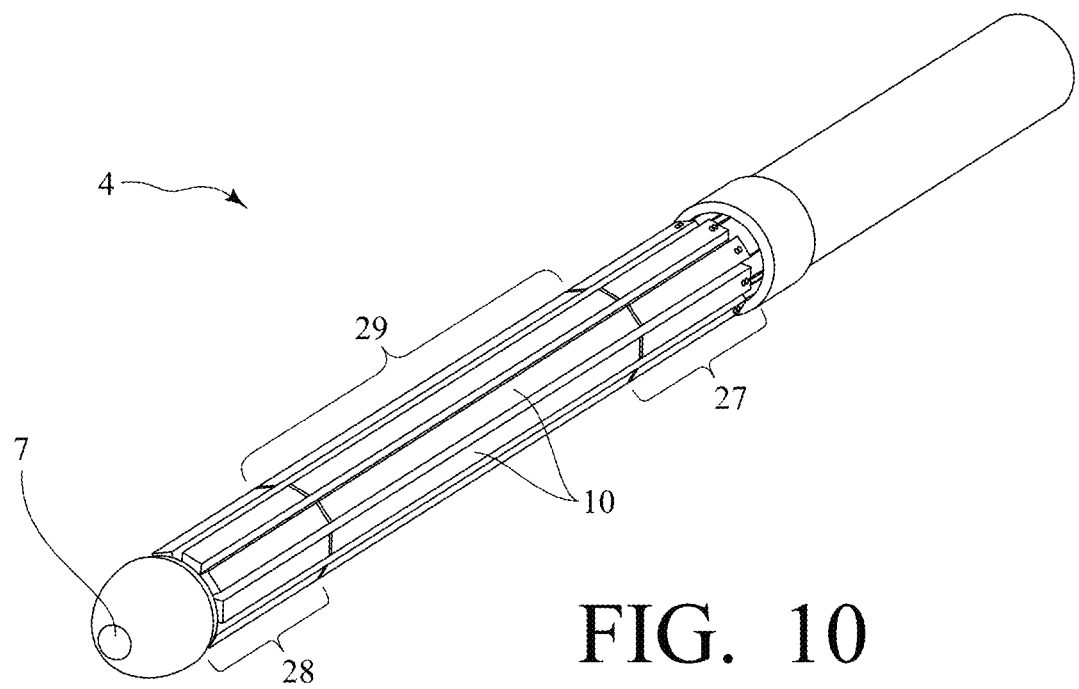
FIG. 10 is a perspective view of another embodiment of an exemplary thermal ablation applicator.

FIG. 10 shows, in yet another embodiment of the invention, an exemplary thermal ablation applicator 4 having a similar shape and dimensions to the exemplary thermal ablation applicator 4 of FIG. 8. The exemplary thermal ablation applicator 4 is having different active portions that comprise equal number of transducer arrays 10, from the proximal to distal end of the applicator there are preferably and respectively portions 27, 29 and 28 that are mounted in adjacent manner. Portion 29 is dedicated to thermal ablation operations as previously described and the portions 27 and 28 can be equipped with other type of sensors or detectors provided that they can be micro manufactured on substrates compatible with the dimensions herein required. As an example, CMUTs are mainly fabricated on a Si substrate, as are other sensors such as: pressure sensors, targeted biosensors (enzymes, antibodies and nucleic acids), chemical sensors, temperature sensors, and micro arrays of electrodes. In the exemplary thermal ablation applicator 4, portions 27 and 28 can be provided with any of the previously mentioned sensors to complete the instrument upon clinical requirements or needs.

In still yet another embodiment (not shown but described with reference to FIG. 10) wherein only either portion 27 or portion 28 is included in the applicator 4, portion 29 is still present for thermal ablation and the portion 27 or portion 28 is equipped with chemical sensors to measuring physiological parameters of the tissue in contact.

Figure 11:
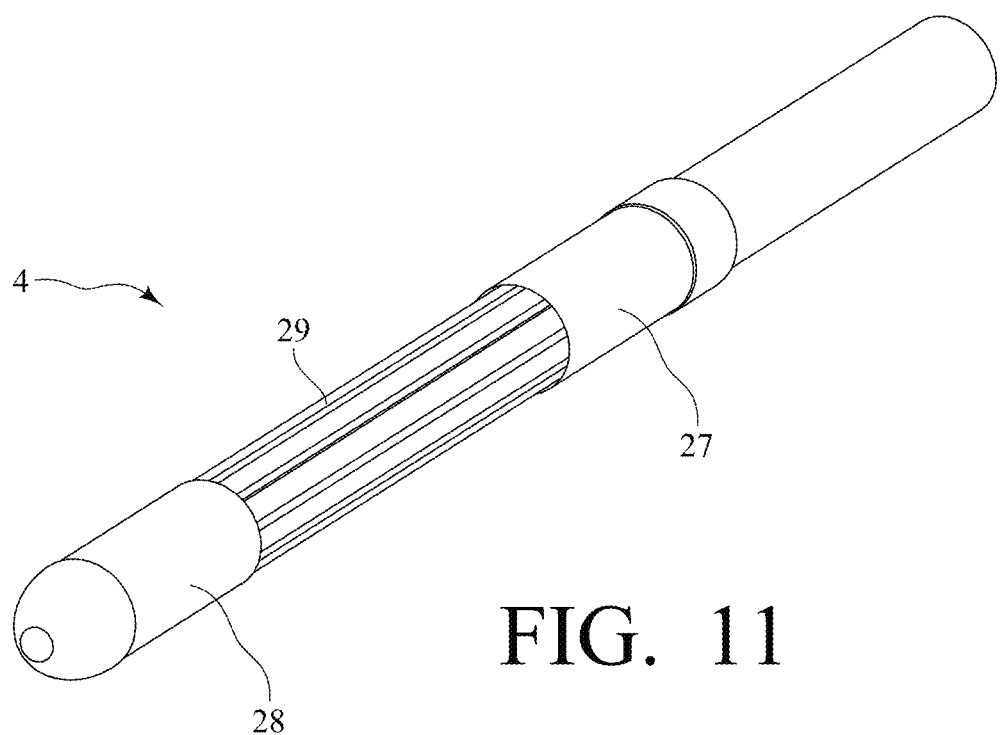
FIG. 11 is a perspective view of another embodiment of an exemplary thermal ablation applicator.

FIG. 11 shows, in yet one further embodiment, an exemplary thermal ablation applicator 4 including thermal ablation operations portion 29, as well as portion 27 and portion 28. Portion 27 and portion 28 comprise integrated nano laser oscillator emitters to allow in vivo sub-cellular tissue identification by near-infrared multi photon-induced auto fluorescence microscopy. To allow photo sensitive nanoparticle delivery, the nano laser oscillator emitters are located on the periphery of portion 27 and/or portion 28 to dispatch light energy to the surrounding structure

What is claimed is:

1. An interstitial ultrasound thermal ablation applicator to be inserted into an inhomogeneous tumor lesion for conformal volume ablation treatment of the inhomogeneous tumor lesion, comprising:
   a body having a longitudinal needle shape and a longitudinal axis, the body including eight to twelve faces regularly disposed on its periphery to form a polygonal shape;
   eight to twelve linear array transducers externally mounted on the respective faces of said body, arranged side by side, having azimuth directions parallel to the longitudinal axis of the body, and having outer faces disposed in a polygonal arrangement, each of the linear array transducers having a flat shape, the linear array transducers being capacitive micromachined ultrasonic transducer (CMUT) array transducers; and
   a power management system electrically connected to the linear array transducers, the power management system controlling the CMUT array transducers to perform the conformal volume ablation treatment when inserted into the inhomogeneous tumor lesion by adjusting depth of treatment with operating frequency, the power management system controlling the CMUT array transducers using Frequency Modulation over a broad continuous spectrum as a function of targeted tissue depths, the power management system controlling the CMUT array transducers to emit multiple ultrasound beams at various frequencies over the broad continuous spectrum to perform the conformal volume ablation treatment;
   the linear array transducers having predetermined width dimensions defined for directing emitted sound waves to obtain the conformal volume ablation treatment of the tumor lesion,
   wherein the emitted sound waves from the linear array transducers have a standard wavelength as measured in water as a propagation medium, and wherein the predetermined width dimensions of the linear array transducers do not exceed three (3) standard wavelengths of the emitted sound waves as measured in water as the propagation medium; and wherein an operating frequency range of the sound waves is from 3 MHz to less than 10 MHz.

2. The interstitial ultrasound thermal ablation applicator according to claim 1, further comprising an electrically insulating protective layer covering the linear array transducers.

3. The interstitial ultrasound thermal ablation applicator according to claim 1, further comprising a biocompatible protection film covering the body and the linear array transducers.

4. The interstitial ultrasound thermal ablation applicator according to claim 1, further comprising an integrated Lab-on-Chip (LoC) device located within a surface of one of the linear array transducers for in-situ analyzing of tissue.

5. The interstitial ultrasound thermal ablation applicator according to claim 1, wherein the body further defines a hollow central channel along the longitudinal axis, the hollow central channel serving as a passage for biopsy needles or tools for aspiration of biologic materials or providing in-situ drug delivery.

6. The interstitial ultrasound thermal ablation applicator according to claim 1, wherein the applicator has a diameter of 3 mm-4 mm.

7. The interstitial ultrasound thermal ablation applicator according to claim 1, wherein a thickness of the linear array transducers is less than 100 microns.

* * * * *